US011213203B2

(12) United States Patent
Mandel et al.

(10) Patent No.: US 11,213,203 B2
(45) Date of Patent: *Jan. 4, 2022

(54) IMPLANTABLE MICRO-FLUIDIC DEVICE FOR MONITORING OF INTRA-OCULAR PRESSURE

(71) Applicant: The Board of Trustees of the Leland Stanford Junior University, Palo Alto, CA (US)

(72) Inventors: Yosef Mandel, Givataim (IL); Ismail Emre Araci, Santa Clara, CA (US); Stephen R. Quake, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 376 days.

This patent is subject to a terminal disclaimer.

(21) Appl. No.: 16/031,044

(22) Filed: Jul. 10, 2018

(65) Prior Publication Data

US 2018/0317768 A1    Nov. 8, 2018

Related U.S. Application Data

(63) Continuation of application No. 14/771,576, filed as application No. PCT/US2014/019660 on Feb. 28, 2014, now Pat. No. 10,016,132.

(Continued)

(51) Int. Cl.
*A61B 90/00* (2016.01)
*A61B 3/16* (2006.01)
*A61B 5/00* (2006.01)

(52) U.S. Cl.
CPC .............. *A61B 3/16* (2013.01); *A61B 5/6821* (2013.01); *A61B 90/361* (2016.02); *A61B 2576/00* (2013.01)

(58) Field of Classification Search
None
See application file for complete search history.

(56) References Cited

U.S. PATENT DOCUMENTS 5,433,701 A    7/1995  Rubinstein
5,671,737 A    9/1997  Harosi
(Continued)

OTHER PUBLICATIONS

Lin et al. 2012. Intraocular pressure sensors: new approaches for real-time intraocular pressure measurement using a purely microfluidic chip. 16th Int. Conf. on Miniaturized Systems for Chemistry and Life Sciences, Oct. 28, 2012.

*Primary Examiner* — Sean P Dougherty
*Assistant Examiner* — Benjamin S Melhus
(74) *Attorney, Agent, or Firm* — Lumen Patent Firm (57) ABSTRACT

Glaucoma is the second most common cause of blindness in the global world. It is a multifactorial disease with several risk factors, of which intraocular pressure (IOP) is the most important. IOP measurements are used for glaucoma diagnosis and patient monitoring. IOP has wide diurnal fluctuation, and is dependent on body posture, so the occasional measurements done by the eye care expert in clinic can be misleading. We provide an implantable sensor, based on microfluidic principles, which in one example has 1 mmHg limit of detection, high sensitivity and excellent reproducibility. This sensor has an optical interface, which enables IOP to be read with, for example, a cell phone camera. The design, fabrication, along with the option of self-monitoring are promising steps toward better patient care and treatment for this devastating disease.

1 Claim, 9 Drawing Sheets

Related U.S. Application Data

(60) Provisional application No. 61/773,963, filed on Mar. 7, 2013.

(56) References Cited

U.S. PATENT DOCUMENTS

| | | | |
|---|---|---|---|
| 6,010,461 | A | 1/2000 | Haniff |
| 6,575,026 | B1 | 6/2003 | Debar |
| 7,252,006 | B2 | 8/2007 | Tai |
| 7,452,075 | B2 | 11/2008 | Iuliano |
| 8,246,569 | B1 | 8/2012 | Meng |
| 2005/0268722 | A1* | 12/2005 | Tai ............ A61B 3/16 73/715 |
| 2008/0058632 | A1* | 3/2008 | Tai ............ G01L 9/0072 600/398 |
| 2009/0069648 | A1 | 3/2009 | Irazoqui |
| 2009/0096988 | A1 | 4/2009 | Fink |
| 2012/0302861 | A1* | 11/2012 | Marshall ............ A61B 3/16 600/398 |
| 2013/0055819 | A1* | 3/2013 | Yan ............ A61B 3/16 73/705 |
| 2014/0046439 | A1* | 2/2014 | Santos ............ A61B 3/16 623/6.22 |

\* cited by examiner

IMPLANTABLE MICRO-FLUIDIC DEVICE FOR MONITORING OF INTRA-OCULAR PRESSURE

CROSS-REFERENCE TO RELATED APPLICATIONS

This application is a continuation of U.S. patent application Ser. No. 14/771,576 filed Aug. 31, 2015 (U.S. patent Ser. No. 10/016,132 issued Jul. 10, 2018), which is incorporated herein by reference.

U.S. patent application Ser. No. 14/771,576 filed Aug. 31, 2015 (U.S. patent Ser. No. 10/016,132 issued Jul. 10, 2018) is a 371 of PCT/US2014/019660 filed on Feb. 28, 2014.

PCT/US2014/019660 filed on Feb. 28, 2014 claims the benefit of U.S. provisional application 61/773,963 filed on Mar. 7, 2013.

FIELD OF THE INVENTION

This invention relates to micro-fluidic intra-ocular pressure monitoring devices, systems and methods. In particular, the invention relates to passive intra-ocular pressure monitoring implants with an external readout mechanism.

BACKGROUND OF THE INVENTION

Glaucoma affects more than 65 million people worldwide and is expected to affect about 80 million people in 2020. It is second only to cataracts in frequency of causing blindness in the global world. Glaucoma is characterized by a progressive loss of retinal ganglion cells, a characteristic optic neuropathy and patterns of visual field loss in the more advanced stages. The pathogenesis of glaucoma is multifactorial with several recognized risk factors of which increased intraocular pressure (IOP) is the most important one.

Normal IOP ranges between 10 to 21 mmHg with an average of 15.3 mmHg. Lowering IOP by medications or surgery is the only therapeutic modality currently available. Therefore, IOP measurements are of great importance for glaucoma diagnosis, management and follow-up during medical or after surgical treatment.

The most widely used method of measuring IOP is Goldmann applanation tonometry (GAT), which is performed by measuring the force required to flatten a pre-defined area of the cornea with a hard surface device. Unfortunately, the accuracy of IOP measurements by GAT is affected by several factors such as corneal thickness as well as other corneal biomechanical properties. Aside from measurement errors, another major drawback of the GAT method is the complexity of the technique. There is also a need for topical anesthesia since the applanator is in direct contact with patient's cornea. Obviously, this procedure cannot be performed by the patients themselves, their relatives or by any other non-professional personnel, and cannot be done routinely in the supine position.

Accordingly, it is clear that since IOP is highly fluctuating, occasional measurements of IOP in the clinicians' office are not sufficient for glaucoma management and there is a need to develop technology that will enable more frequent or home monitoring of IOP in selected cases of glaucoma patients. The present invention addresses this need.

SUMMARY OF THE INVENTION

An intra-ocular pressure sensor is provided to enhance the process of measuring and monitoring of intra-ocular pressure. In a first embodiment, the intra-ocular pressure sensor is based on microfluidic principles and distinguishes a channel with a first open end and a second open end connected to a chamber. A gas is disposed in the chamber in such a way that the gas is disposed through the second open end up to a region of the channel. A fluid is disposed from the first open end up to the region of the channel establishing a fluid-gas equilibrium pressure interface within the channel. The inner diameter of the channel is sized to be capable of holding the fluid within the channel according to capillary forces. The sensor can be configured as an eye implant (e.g. implanted in an intra-ocular lens), where the open end of the channel interfaces with an intra-ocular liquid. The sensor will then be able to measure an intra-ocular pressure based on an established equilibrium pressure interface between the intra-ocular liquid and the gas (i.e. intra-channel fluid and gas equilibrium). Positions along the channel could be added to represent different measures of fluid-gas equilibrium pressure interfaces.

A second embodiment is varied by its configuration and sensing operation compared to the first embodiment. In the second embodiment, the intra-ocular pressure sensor has a channel with a first closed end and a second open end. A chamber is connected to the second open end of the channel and at least part of a chamber wall has a flexible membrane. A fluid is disposed in the chamber and in such a way that it is disposed through the second open end up to a region of the channel. A gas is disposed from the first closed end up to the region of the channel establishing a fluid-gas equilibrium pressure interface within the channel. The intra-ocular pressure sensor is configured to be implantable in an eye and once implanted the membrane would provide an interface between an intra-ocular liquid and the fluid in the chamber. The membrane would flex based on an intraocular pressure therewith establishing an equilibrium pressure interface between the liquid and the gas in the channel.

In a system and method configuration of the sensor, an imaging device, external to the area (or body) of the implant, could be used to obtain an image of the channel. An image analysis computer program could be used to quantify the intra-ocular pressure from the obtained image and the established equilibrium pressure interface. The quantified measure can then be outputted to a user. The program could be executed from the same image device, like a smart phone, or could be executed from a separate or remote computing device that receives the image from the imaging device. The embodiments of the invention are promising steps forward toward better patient care and treatment with more frequent measurements and/or home monitoring.

DETAILED DESCRIPTION

Figure 1:
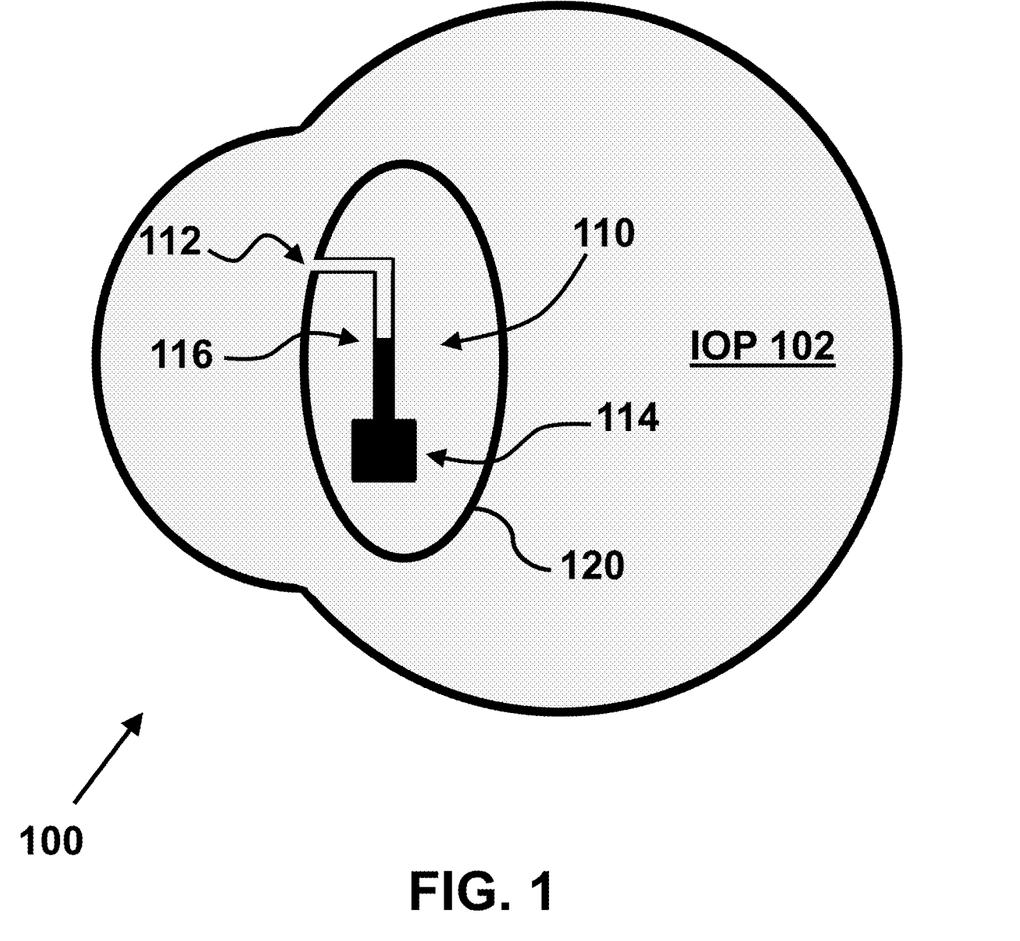
FIG. 1 shows an eye with an intra-ocular monitoring device according to an exemplary embodiment of the invention.

Embodiments of the invention use a passive Intra-Ocular-Pressure (IOP) sensor 110 based on the principles of microfluidic physics to monitor IOP (FIG. 1). The IOP sensor 110 can be chronically implanted into the eye 100 while incorporated in an intraocular lens (IOL) 120, which is routinely used for cataract surgery. Alternatively, it can be implanted as a standalone device in the anterior or posterior chambers of the eye. It can also be installed on a glaucoma drainage device.

In a first embodiment, the IOP sensor has a microfluidic channel 112 open to an aqueous intraocular liquid on one end and connected to a gas chamber or reservoir 114 on the other end (gas is indicated as black for illustration purposes). Capillary forces between the inner wall of the channel and the intraocular liquid and a positive intraocular pressure hold the liquid within at least part of the channel. Increased intraocular pressure 102 would drive the liquid further into the micro-channel 112, compressing the gas inside the reservoir until gas pressure is in equilibrium with liquid pressure as indicated by (gas-fluid) interface 116. Increased intraocular pressure causes the (gas-fluid) interface 116 to shift toward the channel's dead end (the gas reservoir), while decreasing the IOP causes a shift toward the channel opening.

Figure 2:
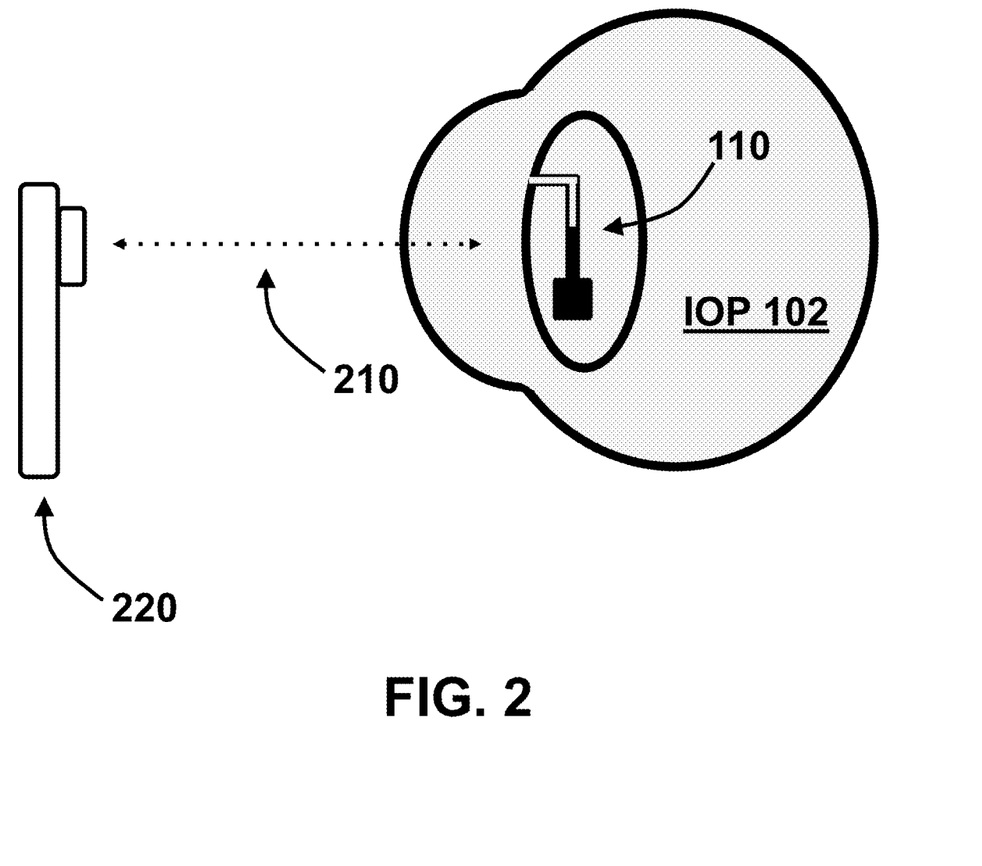
FIG. 2 shows an intra-ocular monitoring system according to an exemplary embodiment of the invention.

Intra-Ocular Pressure readout can be accomplished optically by passing light 210 with wavelength in the range of transparency to the ocular optical media through the eye structures and using a camera 220 to capture an image (FIG. 2). The readout can be performed through a cell phone camera 220, or other camera, equipped with an optical adaptor and image analysis software for detection of the liquid-air/gas interface position. The optical adaptor can be mounted on a cylindrical component designed to position the camera in front of the pupil and shade the eye, therefore eliciting pupil dilatation and exposing the peripherally located sensor. In one example, an iPhone was fitted with a molded plastic aspheric lens with 17 mm focal length or with a bi-convex lens with a 25 mm focal length. Alternatively, the position of the liquid-air/gas interface can be read by other camera-operated systems or easily observed by the ophthalmologist during routine eye examination with a slit lamp.

Figure 3:
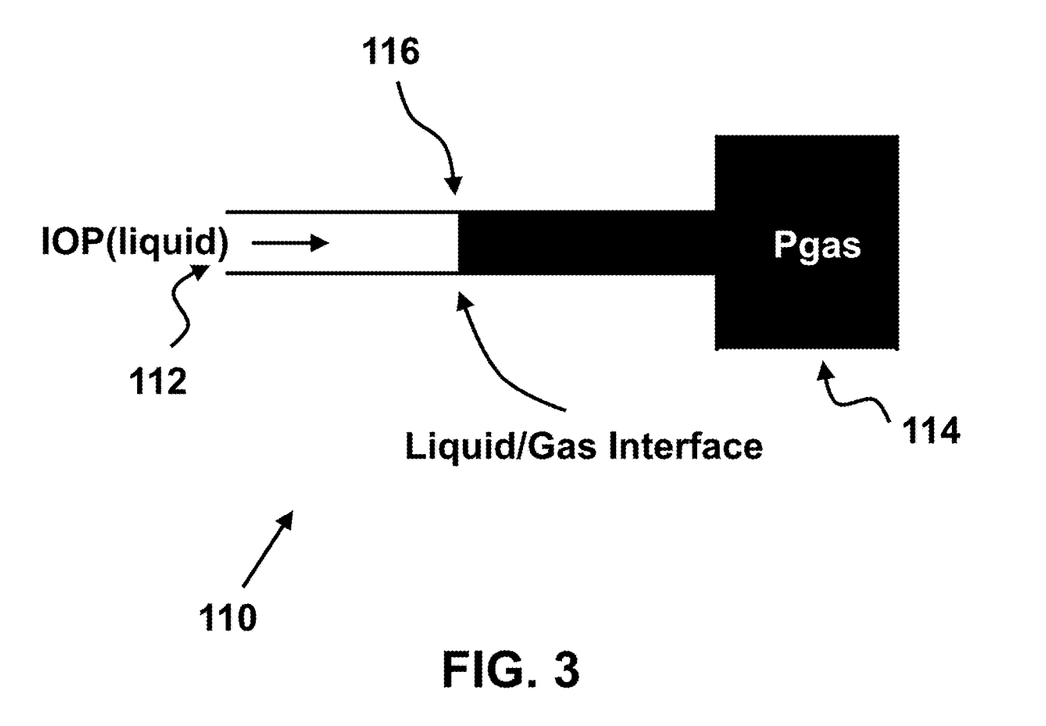
FIG. 3 shows a liquid-air or fluid-gas equilibrium pressure interface according to an exemplary embodiment of the invention.

FIG. 3 shows the operation of the IOP sensor 110. IOP is the liquid pressure, C is the capacitance due to device compliance, $\Delta P_{cap}$ is the capillary pressure drop, R is the fluidic resistance dependent on the channel geometry and $P_{gas}$ is the steady-state gas pressure.

In one example, the sensitivity of the sensor, defined as the displacement of the interface per 1 mmHg change in IOP, is proportional to the ratio between the total channel and reservoir volume to the channel cross section. For example, a sensitivity of about 57 μm/mmHg is expected in an IOP sensor with channel dimensions of 50×50×14,000 μm³ and a reservoir volume of 500×500×300 μm³.

Figure 4:
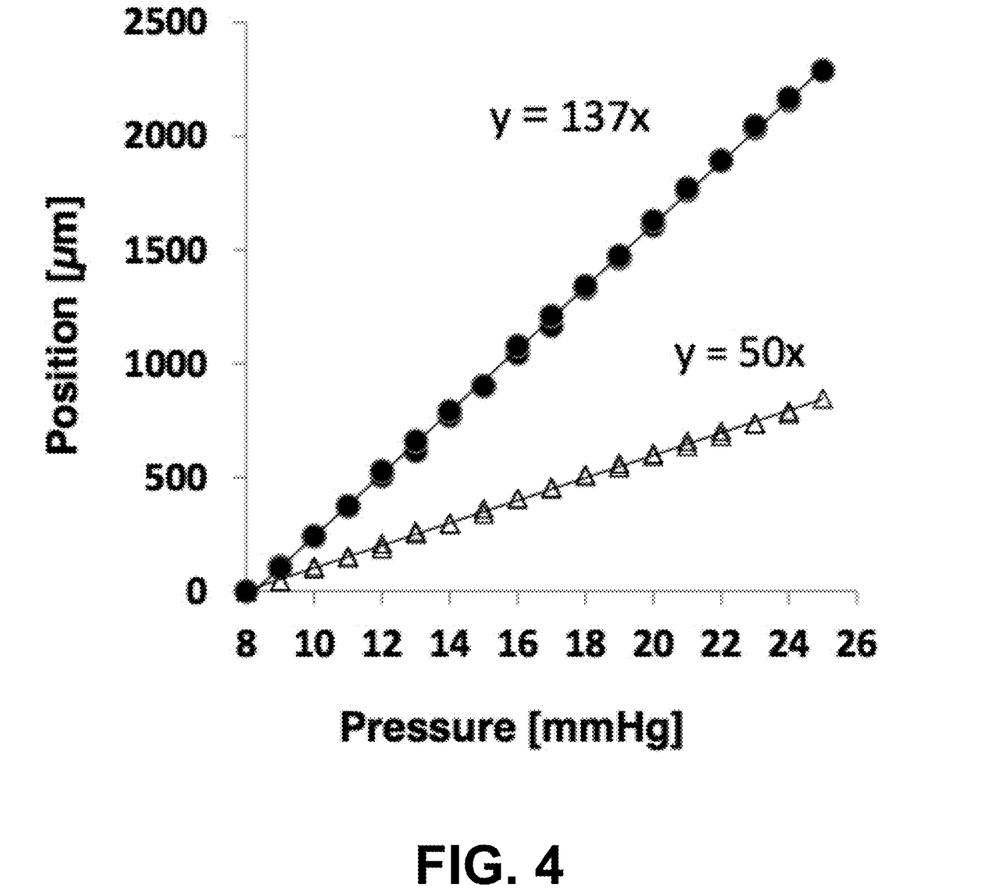
FIG. 4 shows measurements of pressure versus position along the channel according to an exemplary embodiment of the invention.
Figure 5:
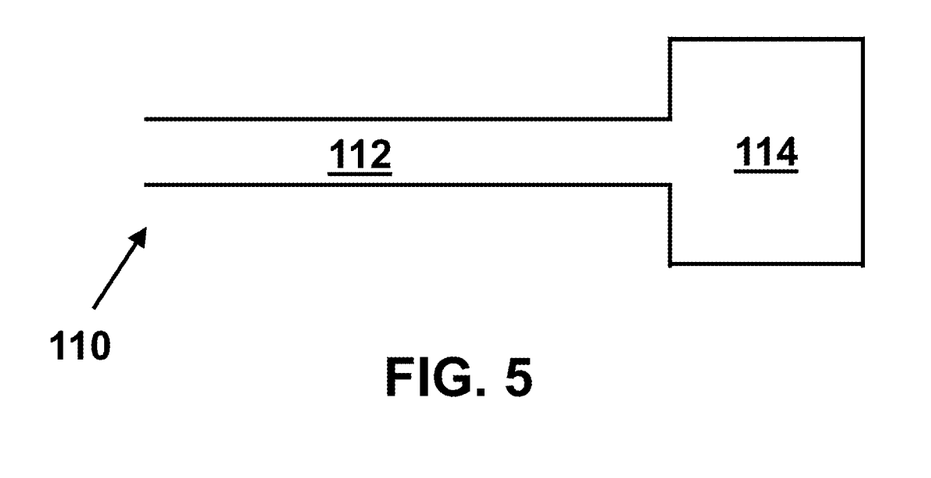
FIGS. 5-7 show different configurations of the device according to exemplary embodiments of the invention.

Calibration of the sensor can be done before implantation by immersing the sensor in a fluid with similar characteristics as the eye fluid (aqueous) and measuring the movement of fluid-gas interface in various fluid pressures. The calibration curve (e.g. FIG. 4) obtained by these measurements can serve for pressure calculation following implantation into the eye. Calibration can also be done post implantation by performing one or more intraocular pressure measurements done by clinically available techniques (such as the Goldman applanation tonometry). These measurements can serve for recalibration if a drift in pressure occurs over the years following implantation.

Figure 6:
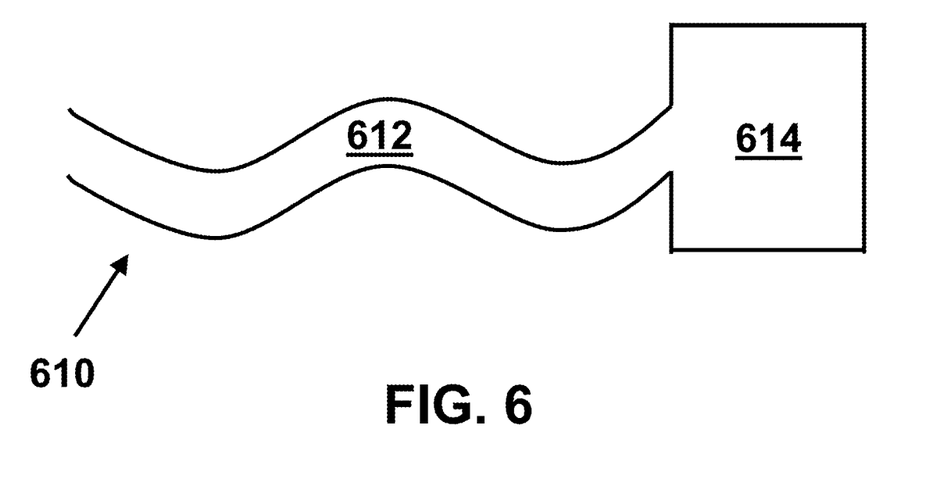
Figure 7:
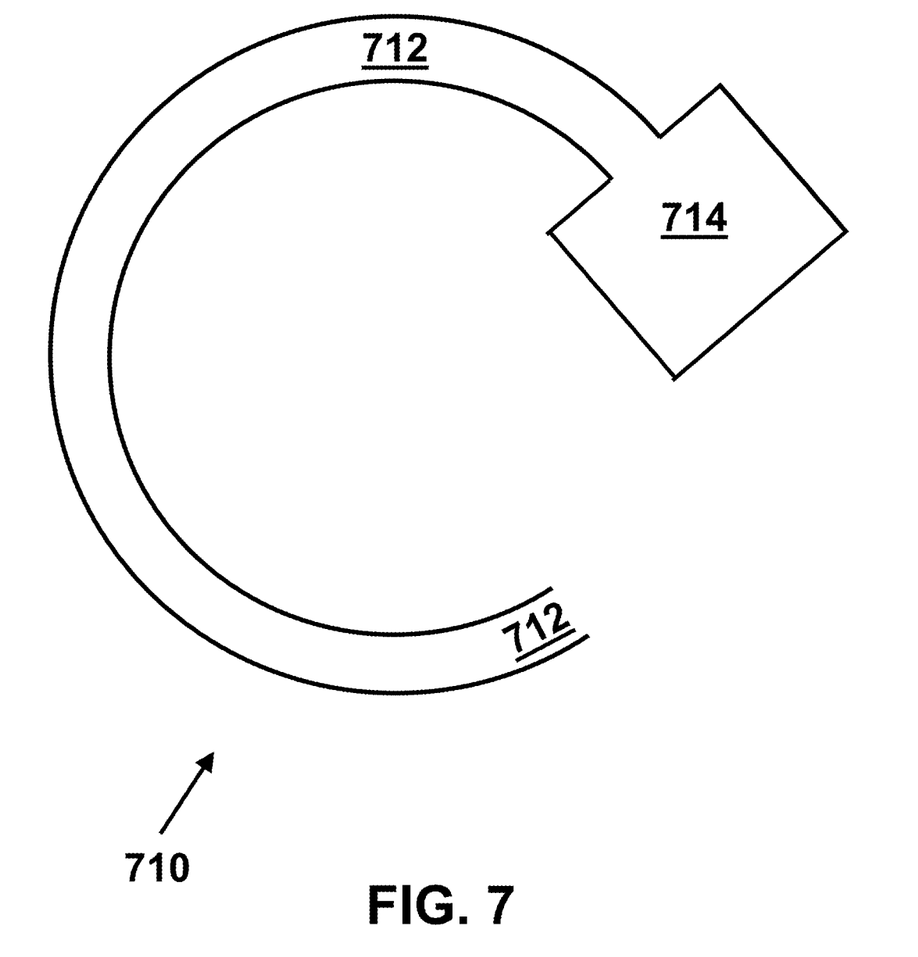
Figure 8:
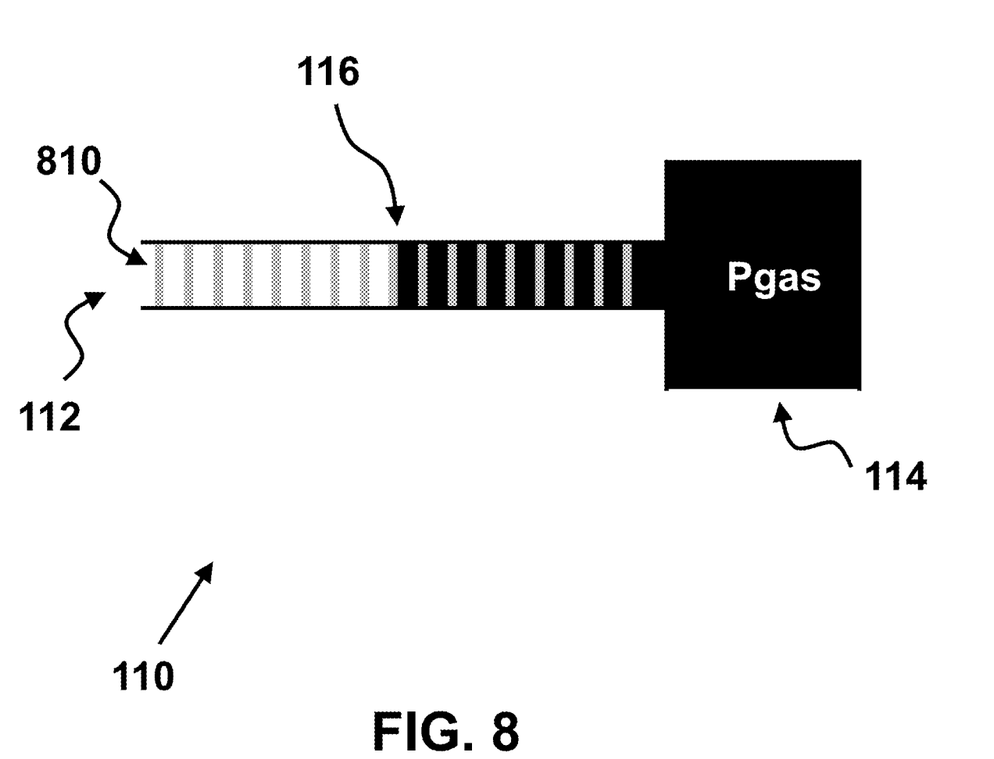
FIG. 8 shows positions or markings along the channel that can be imaged by a camera to measure intra-ocular pressures according to an exemplary embodiment of the invention.

The channels can be filled with one type of fluid or two types with different colors, where the interface between the two liquids can serve as a balance point for measuring IOP. For an example, the fluid could have low friction with the channels walls (e.g. oil) and with any type of gas. Low friction increases sensor sensitivity and decreases hysteresis phenomena. The position of the channels can be in the periphery of the implant (radius>2 mm) in such a way that they are hidden by the pupil and are exposed only when pupil is dilated (e.g. in darkness). The channels can be straight (FIGS. 1-3, 5 (with channel 112 and reservoir 114), serpentine (FIG. 6 with channel 612 and reservoir 614), or circular (FIG. 7 with channel 712 and reservoir 714) (radius of curvature larger than 1 mm and smaller than 12 mm). The inner diameter of the channels can be 1 μm to 300 μm and the channel length can be in the range of 500 to 30 mm. In another example, the inner diameter of the channel can have a 1 to 500 μm by 1 to 500 μm cross-section. The reservoir volume can be 500 by 500 by 300 μm³ or in terms of a range between 3 by 3 by 3 μm³ to 3 by 3 by 3 μm³. The ratio between the reservoir volume to channel cross section is in between 5 μm to $10^4$ μm. The channel walls should preferably have liquid and gas tight structures. Visible positions or marks 810 on the channels are used to enhance readout by the imaging device (FIG. 8).

The intraocular pressure could be transmitted to the intra-channel fluid through one or more openings in the channel or through a thin flexible membrane with a surface area in the range of 100 μm square to 100 mm square as described with respect to a second embodiment of the sensor.

Figure 9:
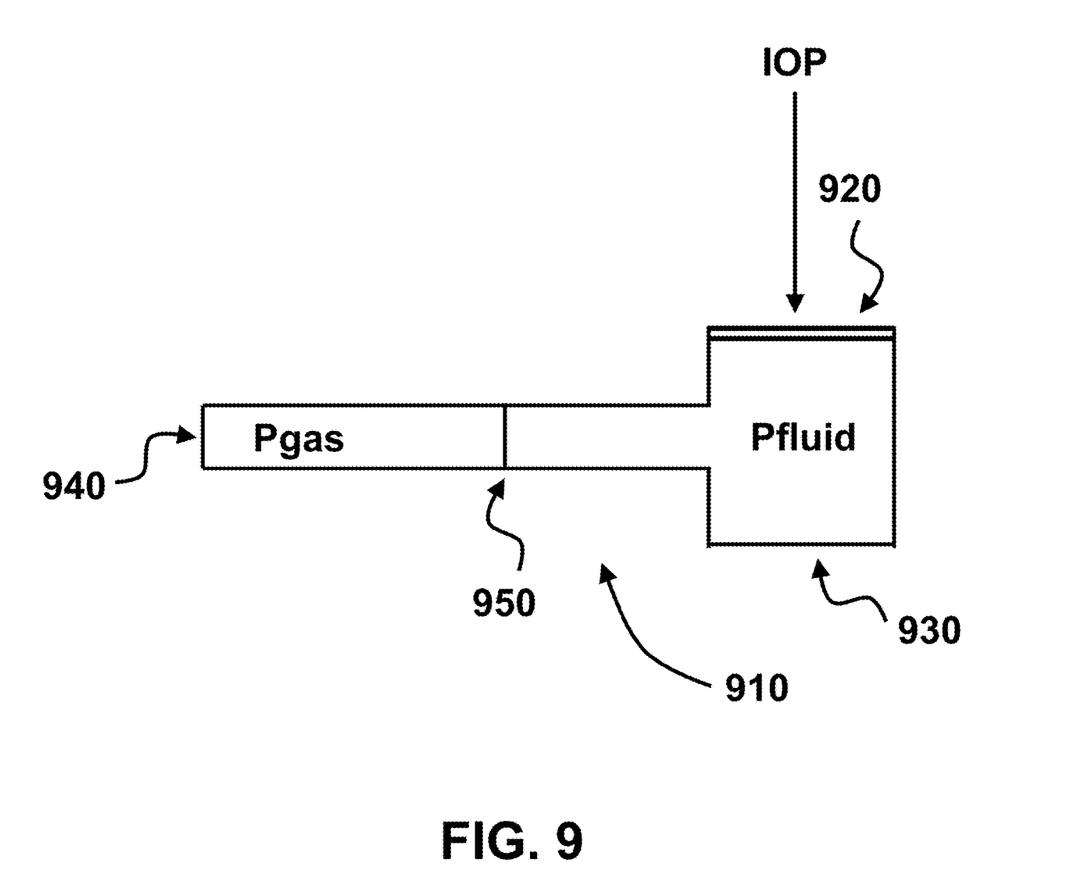
FIG. 9 shows a second embodiment of the intra-ocular monitoring device using a membrane according to an exemplary embodiment of the invention.

In a second embodiment shown in FIG. 9, the IOP sensor 910 has a flexible thin membrane 920 covering a fluid filled reservoir 930, which is connected to a small cross section channel 940 with a dead end. Changes in the IOP cause shifts of fluid volume from the reservoir to the channels and therefore, a movement of the liquid-air (or other gasses) interface 950. Adding color to the fluid in the example could further enhance the visibility of the fluid column (not shown). Alternatively, two fluids with two different colors can be used.

A temperature sensor can be incorporated in the sensor and can be used for pressure correction. Temperature sensor could be incorporated near the IOP sensor or in a separate device.

The readout can be enhanced by using infrared sensitive camera and infrared illumination system which will not induced pupil constriction during imaging. The readout device can be composed on a cylinder or sphere shape construction that will block ambient light to enter the eye thus causing pupil dilation.

Sensitivity Calculation The following description pertains to sensitivity calculation for the first embodiment. When the capillary forces are ignored, the system is in equilibrium in the case of identical liquid and gas pressure values. A step function increase in the liquid pressure disturbs the equilibrium and results in a steady flow towards gas reservoir. The flow continues until the gas pressure becomes equal to liquid pressure. According to the ideal gas law:

$$P_{gas,init} \times V_{gas,init} = P_{gas,final} \times V_{gas,final}$$

When the initial gas pressure is assumed as 1 atmospheric pressure (760 mmHg), the sensitivity, defined as displacement of the interface position in response to 1 mmHg pressure change, can be derived from this as:

$$S = \frac{1}{761} \times \frac{V_{res}}{A_{ch}} \left(1 + \frac{V_{ch}}{V_{res}}\right)$$

where $V_{res}$, $A_{ch}$ and $V_{ch}$ are reservoir volume, channel cross section and channel volume respectively. When reservoir volume is much greater than the channel volume, sensitivity is simply dependent on the ratio between reservoir volume and channel cross section.

In the more realistic case, the capillary effects and system compliance has to be taken into account. For a qualitative understanding of the role of these factors, we have used the equivalent circuit of the sensor inside a pressure chamber (circuit FIG. 10). The liquid pressure, P is the only variable in this circuit model and C is the capacitance due to device compliance, $\Delta P_{cap}^{fw,bw}$ are the capillary pressure drop in forward and backward directions, R is the fluidic resistance dependent on the channel geometry and $P_{gas}$ is the steady-state gas pressure.

Figure 10:
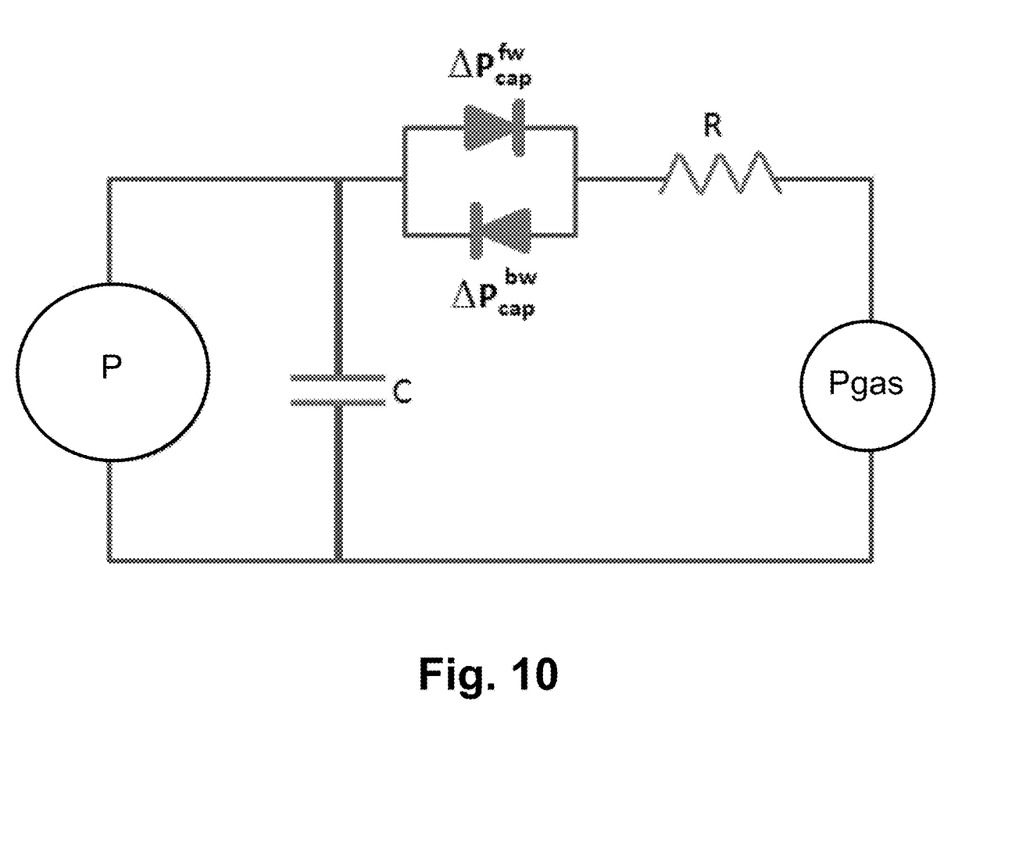
FIG. 10 shows an equivalent scheme of the concept of the intra-ocular monitoring device according to an exemplary embodiment of the invention. P is the liquid pressure, C is the capacitance due to device compliance, $\Delta P_{cap}^{fw,bw}$ are the capillary pressure drop in forward and backward directions, R is the fluidic resistance dependent on the channel geometry and $P_{gas}$ is the steady-state gas pressure.

It can be seen in the equivalent circuit model that, sensitivity (corresponds to fluidic flow and it is analogous to the integral of the current passing through the resistance R over time) will be reduced due to capillary pressure drop, $\Delta P_{cap}^{bw,fw}$ and capacitive effects of device compliance, C). We attribute the discrepancy between measured and theoretical sensitivity values to these factors. Besides the reduced sensitivity, the capillary effects cause a nonlinear behavior when they have positive values (hydrophobic surface) because in this case, pressure change required to move the interface has to be greater than $\Delta P_{cap}^{bw,fw}$ and thus indicated by a diode in the equivalent circuit. To eliminate the nonlinear behavior, the channel surfaces has to be rendered hydrophilic or equivalently channels has to be filled with a high lubricity liquid, in which cases $\Delta P_{cap}^{bw,fw}$ will become negative and degrading effects of the capillary pressure drop can be ignored.

Implantation In case where the sensor is embedded in an intraocular lens, it is implanted in the eye during a routine cataract surgery. The sensor can be implanted independently in the anterior chamber of the eye through a corneal or sclera wound and fixed into the iris or other part of the anterior chamber. Alternatively, the sensor can be implanted into the posterior chamber of the eye through corneal or sclera wound and fixed in the lens capsular bad or other locations.

With respect to the first embodiment, the sensor is filled with the desired gas in a gas chamber, which is held at an atmospheric pressure. Then the sensor is placed inside the desired liquid while it is still inside the gas chamber, therefore the gas is sealed inside the reservoir. Then the sensor is implanted into the eye as explained above. The surface energy between the liquid and sensor prevents the liquid from leaving the sensor.

What is claimed is:

1. An intra-ocular pressure monitoring system, comprising:
   (a) an intra-ocular monitoring device comprising:
      (i) a gas impermeable channel with a first closed end and a second open end;
      (ii) a gas-tight impermeable chamber connected to the second open end of the gas impermeable channel and at least part of a gas impermeable chamber wall has a flexible membrane, wherein the gas impermeable channel and the gas impermeable chamber are made from a gas impermeable material which could be the same or different from each other;
      (iii) a fluid disposed in the gas impermeable chamber and disposed through the second open end up to a region of the gas impermeable channel; and
      (iv) a gas disposed from the first closed end up to the region of the gas impermeable channel establishing a fluid-gas equilibrium pressure interface within the gas impermeable channel,
      wherein the intra-ocular pressure monitoring device is configured to be implantable in an eye, wherein the flexible membrane is an interface between an intra-ocular liquid and the fluid in the gas impermeable chamber, wherein the intra-ocular liquid and the flexible membrane are configured such that the flexible membrane is configured to flex based on a pressure from the intra-ocular liquid, causing a change in the position of the gas-fluid interface until a pressure equilibrium is achieved between the gas, contained in the gas impermeable closed-end channel and the gas impermeable chamber, and the fluid in the closed channel end, wherein the position of the fluid-gas interface is affected by the pressure applied on the flexible membrane and is therefore used for measuring an intra-ocular pressure;
   (b) a camera to obtain an image of the gas-fluid interface; and
   (c) an output quantifying the intra-ocular pressure from the obtained image and the equilibrium pressure interface to a user.

* * * * *